United States Patent [19]

Hampson et al.

[11] 4,434,090
[45] Feb. 28, 1984

[54] DETERGENT COMPOSITIONS CONTAINING SULPHOSUCCINATE MIXTURES

[75] Inventors: Jeffrey D. Hampson; Reginald Billington; Ian R. Cox, all of Merseyside, England

[73] Assignee: Lever Brothers Company, New York, N.Y.

[21] Appl. No.: 400,829

[22] Filed: Jul. 22, 1982

[30] Foreign Application Priority Data

Jul. 24, 1981 [GB] United Kingdom ................ 8122975
Oct. 5, 1981 [GB] United Kingdom ................ 8130062

[51] Int. Cl.$^3$ .......................... C11D 1/83; C11D 1/12
[52] U.S. Cl. .................... 252/547; 252/548; 252/550; 252/551; 252/552; 252/554; 252/555; 252/558; 252/557; 252/DIG. 14
[58] Field of Search ............... 252/538, 557, DIG. 14, 252/DIG. 13, 353, 550, 551, 552, 554, 555, 558, 547, 548; 560/151

[56] References Cited

U.S. PATENT DOCUMENTS

| | | | |
|---|---|---|---|
| 2,028,091 | 1/1936 | Jaeger | 252/557 X |
| 2,265,944 | 12/1941 | Langhorst et al. | 560/151 |
| 2,702,818 | 2/1955 | Jaquay | 560/151 X |
| 2,813,078 | 11/1957 | Vitalis | 252/557 X |
| 3,033,896 | 5/1962 | Anderson | 560/151 |
| 3,043,706 | 7/1962 | Fair et al. | 106/287 |
| 4,072,632 | 2/1978 | Reed | 252/541 |

FOREIGN PATENT DOCUMENTS

1041540 9/1966 United Kingdom .

*Primary Examiner*—P. E. Willis, Jr.
*Attorney, Agent, or Firm*—Milton L. Honig; James J. Farrell

[57] ABSTRACT

A detergent composition with especially good foaming properties includes a di($C_7$–$C_9$) alkyl sulphosuccinate, preferably a di($C_8$ alkyl) sulphosuccinate, and an unsymmetrical dialkyl sulphosuccinate in which one alkyl group is $C_7$–$C_9$ and the other is $C_3$–$C_6$, preferably a ($C_6$ alkyl) ($C_8$ alkyl) sulphosuccinate. A di($C_3$–$C_6$) alkyl sulphosuccinate may advantageously be present. An especially preferred mixture comprises di(n-octyl), (n-octyl n-hexyl) and di(n-hexyl) sulphosuccinates, and this mixture may be prepared by esterifying maleic anhydride or the like with a mixture of n-octanol and n-butanol, followed by bisulphite addition. The detergent composition is preferably in liquid form and is suitable for shampoos, fabric washing and, in particular, manual dishwashing.

23 Claims, No Drawings

DETERGENT COMPOSITIONS CONTAINING SULPHOSUCCINATE MIXTURES

The present invention relates to certain detergent-active materials, and to their use in detergent compositions suitable for many purposes, for example, fabric washing products, general purposes domestic and industrial cleaning compositions, products, shampoos, foam bath products and, above all, compositions for use in manual dishwashing operations in both hard and soft water.

The term "dishes" as used herein means any utensils involved in food preparation or consumption which may be required to be washed to free them from food particles and other food residues, greases, proteins, starches, gums, dyes, oils and burnt organic residues.

Light-duty liquid detergent compositions such as are suitable for use in washing dishes are well known. Most of the formulations in commercial use at the present time are based on anionic synthetic detergents with or without a nonionic detergent. Many of such formulations contain a sulphonate-type anionic detergent, for example, an alkylbenzene sulphonate or an alkane sulphonate, in conjunction with a sulphate-type anionic detergent, for example, an alkyl sulphate or an alkyl ether sulphate, or a nonionic detergent, for example, an alcohol ethoxylate, an alkyl phenol ethoxylate, a mono- or diethanolamide or an amine oxide. The sulphonate material generally predominates.

Alkylbenzene sulphonates and alkane sulphonates are produced by sulphonation of petrochemically derived hydrocarbons and consist of a mixture of materials of different chain lengths and sulphonate group substitution, only some of which contribute to the cleaning and foaming performance of the product, different materials being useful at different water hardnesses. The chemistry of manufacture of these materials allows at best limited control of the isomer distribution in the product alkylbenzene sulphonates and secondary alkane sulphonates.

GB No. 1,429,637 (Unilever) discloses hand dishwashing compositions containing as detergent-active material a water-soluble salt of a di($C_7$–$C_9$)alkyl ester of sulphosuccinic acid, in combination with an alkyl sulphate or an alkyl ether sulphate. These compositions show good foaming and cleaning properties which are sharply dependent on the chain length of the dialkyl sulphosuccinates, the di(n-$C_6$) and di(n-$C_{10}$) compounds giving very poor results compared with the di($C_7$–$C_9$) compounds.

It has now surprisingly been found that certain combinations of dialkyl sulphosuccinates of particular chain length, including as an essential component some material containing a shorter chain ($C_6$ or less), show unexpectedly good foaming and cleaning performance.

These combinations of sulphosuccinates may be used, alone or together with other detergent-active agents, to form the basis of highly efficient detergent compositions, especially liquid detergent compositions, which are suitable inter alia for hand dishwashing.

The present invention accordingly provides a detergent composition, more especially a liquid detergent composition, comprising (a) one or more compounds of the formula I:

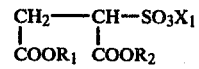

wherein each of $R_1$ and $R_2$, which may be the same or different, represents an alkyl group having from 7 to 9 carbon atoms, and $X_1$ represents a solubilising cation, and (b) one or more compounds of the formula II:

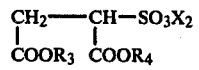

wherein one of $R_3$ and $R_4$ represents an alkyl group having from 7 to 9 carbon atoms and the other represents an alkyl group having from 3 to 6 carbon atoms, and $X_2$ represents a solubilising cation which may be the same as or different from $X_1$.

Preferably the total number of carbon atoms in the two groups $R_3$ and $R_4$ is at least 11, more preferably at least 12.

By "solubilising cation" is meant any cation yielding a salt of the formula I or II sufficiently soluble to be detergent active. The solubilising cations $X_1$ and $X_2$ will generally be monovalent, for example, alkali metal, especially sodium; ammonium; or substituted ammonium, for example, ethanolamine. However, certain divalent cations, notably magnesium, are also suitable.

For convenience the compounds (a) and (b) will be hereinafter referred to as merely as dialkyl sulphosuccinates, but it is to be understood that this term is intended to refer to the salts of solubilising cations.

The proportions of the two components (a) and (b) in the detergent composition of the invention are not critical. In principle the mole ratio of (a) to (b) can range from 99:1 to 1:99, preferably from 10:1 to 1:10; (a):(b) ratios of less than 1:1, especially less than 1:2, give especially good results.

The R groups in the compounds (a) and (b) may be straight-chain or branched-chain. Compounds in which at least one of the R groups is a straight-chain alkyl group are especially preferred.

Where a branched-chain group is present, the number of carbon atoms mentioned in the definitions of the compounds (a) and (b) above may refer either to the total number of carbon atoms or to the number of carbon atoms in the longest chain present.

Mixtures of straight-chain and branched-chain material may if desired be used.

Advantageously compound (a) is symmetrical, that is to say, both R groups are the same. The symmetrical compounds encompassed by the formula I are as follows:

di($C_7$ alkyl) sulphosuccinate,
e.g. di(n-heptyl) sulphosuccinate
di($C_8$ alkyl) sulphosuccinate,
e.g. di(n-octyl) sulphosuccinate, di(2-methylheptyl) sulphosuccinate
di($C_9$ alkyl) sulphosuccinate,
e.g. di(n-nonyl) sulphosuccinate, di(2-methyloctyl) sulphosuccinate.

If desired, however, a compound (a) with two different R groups may be employed. The unsymmetrical compounds encompassed by the formula I are as follows:

($C_7$ alkyl) ($C_8$ alkyl) sulphosuccinate ($C_7$ alkyl) ($C_9$ alkyl) sulphosuccinate
($C_8$ alkyl) ($C_9$ alkyl) sulphosuccinate.

Since the two R groups are not in equivalent positions, two isomers of each of the above compounds exist. The invention encompasses the use of either or both isomers in each case.

Compounds of the formula I in which the R groups have 7 or 8 carbon atoms, that is to say
di($C_7$ alkyl) sulphosuccinate
di($C_8$ alkyl) sulphosuccinate
($C_7$ alkyl) ($C_8$ alkyl) sulphosuccinate are preferred for use in the invention.

Compounds of the formula I in which the R groups have 8 carbon atoms, namely, the di($C_8$ alkyl) sulphosuccinates, are of special interest. The di($C_8$ alkyl) sulphosuccinates are already known to be high foaming detergent-active agents under certain conditions but may suffer from one deficiency in this respect: relatively poor performance in water of hardness greater than about 16°H (French). Surprisingly, however, the performance of those materials in both hard and soft water, but particularly in hard water, has been found to be enhanced, according to the invention, by the admixture of the mixed chain-length material (b) of the formula II, whether or not the latter is itself a high-foaming material.

The compound (b) of the formula II is by definition unsymmetrical, and contains one alkyl chain of comparable chain length to that (or those) of the (a) compound, and one shorter alkyl chain. The compound (b) is selected from the following list:
($C_3$ alkyl) ($C_7$ alkyl) sulphosuccinate
($C_3$ alkyl) ($C_8$ alkyl) sulphosuccinate
($C_3$ alkyl) ($C_9$ alkyl) sulphosuccinate
($C_4$ alkyl) ($C_7$ alkyl) sulphosuccinate
($C_4$ alkyl) ($C_8$ alkyl) sulphosuccinate
($C_4$ alkyl) ($C_9$ alkyl) sulphosuccinate
($C_5$ alkyl) ($C_7$ alkyl) sulphosuccinate
($C_5$ alkyl) ($C_8$ alkyl) sulphosuccinate
($C_5$ alkyl) ($C_9$ alkyl) sulphosuccinate
($C_6$ alkyl) ($C_7$ alkyl) sulphosuccinate
($C_6$ alkyl) ($C_8$ alkyl) sulphosuccinate
($C_6$ alkyl) ($C_9$ alkyl) sulphosuccinate.

Each unsymmetrical member of the list represents a pair of isomers and the invention encompasses the use of either or both isomers in each case.

Preferred chain lengths for the unsymmetrical (b) compound are $C_4$ and $C_6$ for the shorter chain, because of the ready availability of the corresponding starting materials, and $C_7$ and $C_8$ for the longer chain, for performance reasons, thus:
($C_4$ alkyl) ($C_7$ alkyl) sulphosuccinate
($C_4$ alkyl) ($C_8$ alkyl) sulphosuccinate
($C_6$ alkyl) ($C_7$ alkyl) sulphosuccinate
($C_6$ alkyl) ($C_8$ alkyl) sulphosuccinate.

According to one preferred embodiment of the invention, a matched pair of compounds (a) and (b) is chosen such that the longer chain of the compound (b) is of the same length as one, or more preferably both, chains of the compound (a). Thus a di($C_7$ alkyl) sulphosuccinate may be matched with a ($C_3$–$C_6$ alkyl) ($C_7$ alkyl) sulphosuccinate; and, according to an especially preferred embodiment of the invention a di($C_8$ alkyl) sulphosuccinate may be matched with a ($C_3$–$C_6$ alkyl) ($C_8$ alkyl) sulphosuccinate.

Two combinations that have been found to give exceptionally good results are the following:

di($C_8$ alkyl) sulphosuccinate plus ($C_4$ alkyl) ($C_8$ alkyl) sulphosuccinate, and,
di($C_8$ alkyl) sulphosuccinate plus ($C_6$ alkyl) ($C_8$ alkyl) sulphosuccinate.

The ($C_6$ alkyl) ($C_8$ alkyl) sulphosuccinate, which is the subject of our copending application of even date, is itself a high-foaming detergent-active material. Under certain conditions, however, mixtures of di($C_8$ alkyl) and ($C_6$ alkyl) ($C_8$ alkyl) sulphosuccinate gives better foaming performance than either of the constituent materials.

The ($C_4$ alkyl) ($C_8$ alkyl) sulphosuccinate is not, alone, a high-foaming material. Its admixture with di($C_8$ alkyl) material, however, can increase the foaming performance of the latter material.

According to a further preferred aspect of the invention, the detergent composition may additionally comprise one or more compounds (c) of the formula III:

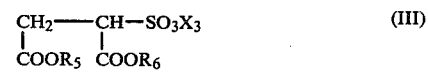

$$\begin{array}{c} CH_2 \text{\textemdash\textemdash} CH \text{\textemdash} SO_3X_3 \\ | \qquad\quad | \\ COOR_5 \quad COOR_6 \end{array} \quad (III)$$

wherein each of $R_5$ and $R_6$, which may be the same or different, represents an alkyl group having from 3 to 6 carbon atoms, and $X_3$ represents a solubilising cation which may be the same as or different from $X_1$ and/or $X_2$.

Preferably the amount of component (c) does not exceed 50 mole percent, based on the total amount of components (a), (b) and (c).

The alkyl groups $R_5$ and $R_6$ may be straight or branched-chain, straight-chain groups being preferred.

The formula III includes the following compounds:
di($C_3$ alkyl) sulphosuccinate
di($C_4$ alkyl) sulphosuccinate
di($C_5$ alkyl) sulphosuccinate
di($C_6$ alkyl) sulphosuccinate
($C_3$ alkyl) ($C_4$ alkyl) sulphosuccinate
($C_3$ alkyl) ($C_5$ alkyl) sulphosuccinate
($C_3$ alkyl) ($C_6$ alkyl) sulphosuccinate
($C_4$ alkyl) ($C_5$ alkyl) sulphosuccinate
($C_4$ alkyl) ($C_6$ alkyl) sulphosuccinate
($C_5$ alkyl) ($C_6$ alkyl) sulphosuccinate.

Symmetrical compounds are preferred, and of these the di$C_4$ and di$C_6$ compounds are of especial interest. The $C_4/C_6$ unsymmetrical compound is also of interest.

According to one embodiment of the invention, the chain length of one, or preferably both, R groups of the (c) compound is the same as that of the shorter R group of the (b) compound. Thus, for example, the (c) compound may be matched to the (b) compound as follows:

| (b) compound | (c) compound |
| --- | --- |
| $C_4/C_7$ | di$C_4$ |
| $C_4/C_8$ | di$C_4$ |
| $C_6/C_7$ | di$C_6$ |
| $C_6/C_8$ | di$C_6$ |

As previously mentioned, the (a) and (b) compounds may themselves advantageously be matched as to chain length. Thus, according to a very advantageous embodiment of the invention, the essential components (a) and (b) and the optional component (c) are all matched to one another with respect to chain length, the (a) and (c) compounds being symmetrical and the (b) compound having chain lengths corresponding to those of the (a) and (c) compounds. Thus, for example:

| (a) | (b) | (c) |
|---|---|---|
| diC$_7$ | C$_4$/C$_7$ | diC$_4$ |
| diC$_8$ | C$_4$/C$_8$ | diC$_4$ |
| diC$_8$ | C$_6$/C$_8$ | diC$_6$ |

The combinations including di(C$_8$ alkyl) sulphosuccinate are of especial interest.

The compounds (a), (b) and (c) used according to the present invention may be prepared by any suitable method. The synthesis of dialkyl sulphosuccinates is well documented in the literature; see, for example, U.S. Pat. No. 2,028,091 (American Cyanamid).

According to a preferred method, maleic anhydride (or maleic acid or fumaric acid, but preferably maleic anhydride) is esterified with an appropriate alkanol, in the presence of an acid catalyst such as p-toluene sulphonic acid, to give the corresponding dialkyl maleate/fumarate, which is then subjected to bisulphite addition to give the dialkyl sulphosuccinate:

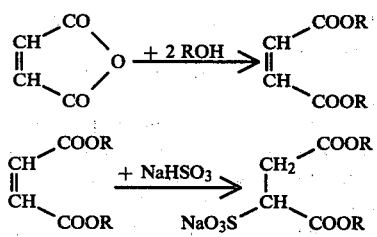

Esterification of maleic anhydride (or maleic acid or fumaric acid) with a single alcohol gives a single product in which both alkyl groups are the same. If, however, a mixture of two alcohols is used, a mixture of products is obtained:

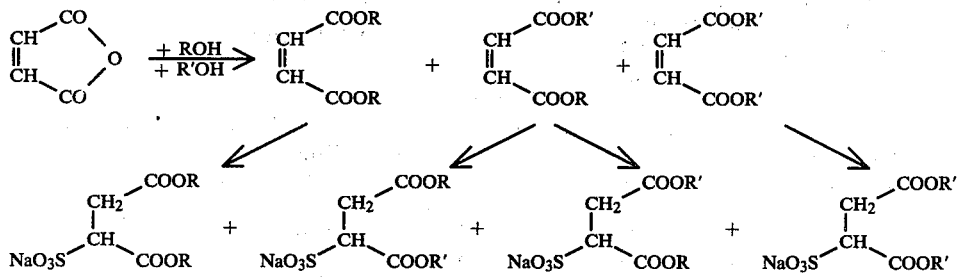

If a substantially equimolar mixture of the two starting alcohols is used, statistically one would expect about 25 mole percent each of the two symmetrical diesters and about 50 mole percent of the unsymmetrical diester (isomer mixture).

If one of the starting alcohols is a C$_7$–C$_9$ alkanol and the other a C$_3$–C$_6$ alkanol, the three products obtained will be compounds (a), (b) and (c) according to the present invention. For example, using n-butanol and n-octanol as starting alcohols, a mixture of di-n-octyl sulphosuccinate, n-butyl n-octyl sulphosuccinate and di-n-butyl sulphosuccinate will be obtained.

Thus, according to a further preferred embodiment of the invention, the sulphosuccinate mixture is obtained by a process which includes the esterification of a suitable starting material, especially maleic anhydride but also maleic acid, fumaric acid or sulphosuccinic acid, with a mixture of a C$_7$–C$_9$ alkanol and a C$_3$–C$_6$ alkanol.

If desired, a mixture of three or more alkanols may be used in the esterification reaction. For example, a mixture of n-butanol, n-hexanol and n-octanol gives the following mixture of sulphosuccinates:
compound (a): di-n-octyl
compounds (b): n-butyl n-octyl, n-hexyl n-octyl
compounds (c): di-n-butyl, di-n-hexyl, n-butyl n-hexyl.
This last mixture gives excellent foaming results.

The foaming performance of the sulphosuccinate mixtures of the invention is generally substantially better than would be expected from the performance of the individual components. It is particularly surprising that mixtures such as that mentioned in the previous paragraph, containing a high proportion of short-chain material, should exhibit a foaming performance similar to that of di-n-octyl sulphosuccinate alone in soft water, and a substantially better performance in hard water.

As indicated previously, dialkyl sulphosuccinates may be manufactured from alkanols, which are commercially available as materials of strictly defined chain length: thus the chain length of the sulphosuccinates may be precisely controlled.

Detergent compositions according to the invention may if desired contain other detergent-active agents as well as the sulphosuccinate mixture of the invention. These are preferably anionic or nonionic, but may also be cationic, amphoteric or zwitterionic. The type of detergent-active material present in addition to the sulphosuccinate mixture of the invention will depend on the intended end-use of the product. The weight ratio of total sulphosuccinate to other detergent-active material may range, for example, from 99:1 to 1:99.

The invention is, as previously mentioned, especially concerned with manual dishwashing compositions, and in these the sulphosuccinate mixture of the invention may if desired be used in conjunction with other anionic detergents, for example, alkylbenzene sulphonates, secondary alkane sulphonates, α-olefin sulphonates, alkyl glyceryl ether sulphonates, primary and secondary alkyl sulphates, alkyl ether sulphates, and fatty acid ester sulphonates; or with nonionic detergents such as ethoxylated and propoxylated alcohols and ethoxylated and propoxylated alkyl phenols. These materials are well-known to those skilled in the art. Materials such as amine oxides and mono- and dialkanolamides, which may be regarded either as nonionic surfactants or as foam boosters, may also be present additionally or alternatively. These materials too are well known to those skilled in the art.

Some of the combinations of detergent-active materials referred to in the two preceding paragraphs will of course be suitable for products other than hand dishwashing compositions.

In formulations intended for hand dishwashing combinations of sulphosuccinates according to the invention with certain other detergent-active materials, notably alkyl ether sulphates and nonionic detergents, are especially preferred. The weight ratio of total sulphosuccinate to these other materials is preferably within the range of from 1:4 to 20:1, more preferably from 1:1 to 12:1. Preferred alkyl ether sulphates are primary and secondary alcohol ethoxy sulphates represented by the general formula $R_1$—O—$(C_2H_4O)_n$—$SO_3M$, in which $R_1$ represents an alkyl group having 10 to 18 carbon atoms, the degree of ethoxylation n is from 1 to 12, and M represents an alkali metal, an ammonium or an amine cation. The $R_1$ group more preferably contains 10 to 15 carbon atoms, and n is more preferably from 1 to 8. In any commercially available ether sulphate, there will of course be a spread of degree of ethoxylation, and n will represent an average value. An example of a suitable amine cation M is the monoethanolamine cation.

Preferred nonionic detergents are in particular the condensates of straight or branched chain primary or secondary aliphatic alcohols with ethylene oxide, of the general formula $R_2$—O—$(C_2H_4O)_mH$, in which $R_2$ is an alkyl group having from 8 to 20 carbon atoms, preferably from 8 to 12 carbon atoms, and m, the average degree of ethoxylation, ranges from 5 to 20.

Other suitable nonionic detergents include nonionic alkylphenol polyethers of the general formula $R_3$—$C_6H_4$—O—$(C_2H_4O)_xH$, where $R_3$ is an alkyl group having from 6 to 16 carbon atoms, preferably 8 to 12 carbon atoms, and the average degree of ethoxylation x is from 8 to 16, preferably 9 to 12; and nonionic condensates of fatty acids and ethylene oxide of the general formula $R_4$—CO—O—$(C_2H_4O)_yH$, where $R_4$ is an alkyl group having from 12 to 18 carbon atoms, and the average degree of ethoxylation y is from 8 to 16.

As previously mentioned, the detergent compositions of the invention are preferably liquids, although the dialkyl sulphosuccinates of the formulae I, II and III are themselves solids at ambient temperature. The detergent compositions of the invention may, however, be in any suitable physical form, for example, powders, solid bars or gels. They may be used for any type of detergent product, for example, fabric washing products, general purpose domestic and industrial cleaning compositions, carpet shampoos, car wash products, personal washing products, shampoos, foam bath products, and mechanical and manual dishwashing compositions.

The sulphosuccinate materials with which the invention is concerned are however outstandingly suitable for incorporation in liquid products, with or without other detergent-active materials. These liquid detergent products may be used for all normal detergent purposes, but are of especial interest for use as fabric washing liquids, both built and unbuilt, for both heavy-duty laundry and for washing delicate fabrics; as shampoos; and, above all, as products for dishwashing, especially for hand dishwashing. These liquid products may range from concentrates, containing virtually 100% active detergent, to the more dilute aqueous solutions seen by the consumer. In the latter type product the total amount of detergent-active material will generally range from 2 to 60% by weight, the balance being made up by water; minor ingredients such as perfume, colour, preservatives, germicides and the like; and, if necessary, a viscosity and solubility control system, referred to in the art as a hydrotrope. The hydrotrope system, for example, may comprise any one or more of the following materials: lower alcohols, especially ethanol; urea; and lower mono- or dialkylbenzene sulphonates, such as sodium or ammonium xylene sulphonates or toluene sulphonates.

The invention is further illustrated by the following non-limiting Examples.

EXAMPLE 1

(i) Preparation of statistical mixture of $C_6/C_8$ maleates/fumarates

Maleic anhydride (98 g, 1 mole) in toluene (400 ml) containing octan-1-ol (130 g, 1.0 mole) and hexan-1-ol (102 g, 1.0 mole) and p-toluene sulphonic acid (2 g) was stirred under reflux for 3 hours. Water was removed azeotropically by means of a Dean & Stark apparatus (approximately 18 ml, i.e. 1 mole, of water were collected). The crude reaction mixture was cooled and washed with 30% sodium hydroxide solution, then water, then brine, before drying over anhydrous magnesium sulphate. The mixture was filtered and the solvents removed in vacuo to yield an oil (293 g). This oil was shown by gas-liquid chromatography coupled with mass spectrometry to consist of the symmetrical di$C_8$ diester, the unsymmetrical $C_6/C_8$ diester and the symmetrical di$C_6$ diester in molar proportions of approximately 1:2:1.

(ii) Preparation of statistical mixture of $C_6/C_8$ sulphosuccinates

The oil prepared in Example 1(i), without further purification, was dissolved in industrial methylated spirit (500 ml) and refluxed with 475 ml of a 40% aqueous solution of sodium metabisulphite for 6 hours. The solvent was removed in vacuo to yield a crude solid which was taken up in hot ethanol, filtered hot, and allowed to crystallise at 0° C. A yield of 300 g was obtained, consisting of about 98% detergent-active material and 0.11% non-detergent organic matter. By high-performance liquid chromatography it was shown to consist of the di$C_8$, $C_6/C_8$ and di$C_6$ dialkyl sulphosuccinates in molar proportions of approximately 1:2:1.

EXAMPLE 2

(i) Preparation of statistical mixture of $C_4/C_8$ maleates/fumarates

The procedure of Example 1(i) was repeated, but with butan-1-ol (74 g, 1.0 mole) replacing the hexanol in the starting alcohol mix. 269 g of oil were obtained.

This oil was shown by gas-liquid chromatography coupled with mass spectrometry to consist of the symmetrical di$C_8$ maleate/fumarate diester, the unsymmetrical $C_4/C_8$ diester and the symmetrical di$C_4$ diester, in molar proportions of approximately 1:2:1.

(ii) Preparation of statistical mixture of $C_4/C_8$ sulphosuccinates

The oil, without further purification, was converted to the corresponding sulphosuccinate mixture by the procedure of Example 1(ii). The product consisted of about 95% detergent-active material and about 1.5% non-detergent organic matter. It was shown by high-performance liquid chromatography to consist of the di$C_8$, $C_4/C_8$ and di$C_4$ sulphosuccinates in molar proportions of approximately 1:2:1.

EXAMPLE 3

(i) Preparation of pure butyl/octyl maleate/fumarate

A statistical mixture of $C_4/C_8$ maleates/fumarates was prepared as described in Example 2(i). The oil obtained (269 g) was subjected to fractional distillation in vacuo to separate the three components. A yield of 60 g of the pure $C_4/C_8$ unsymmetrical maleate/fumarate was obtained. This material had a boiling point of 180°–200° C. (0.2 mm Hg) and infra-red peaks at 1640 cm$^{-1}$ (C=C) and 1725 cm$^{-1}$ (C=O). It was identified also by $^1$H NMR and mass spectrometry.

(ii) Preparation of pure butyl/octyl sulphosuccinate

The product of Example 3(i) (60 g) was converted to the corresponding sulphosuccinate by the procedure of Example 1(ii). The product obtained consisted of 98% detergent-active material and 0.5% non-detergent organic matter. It had infra-red peaks at 1735 cm$^{-1}$ (C=O) and 1210–1240 m$^{-1}$ (SO$_3$Na) and was also identified by $^1$H NMR.

EXAMPLES 4 AND 5

Preparation of pure hexyl/octyl sulphosuccinate

The method of Example 3 cannot be used for the $C_6/C_8$ system, because the boiling points of the diC$_6$, diC$_8$ and $C_6/C_8$ maleate/fumarate diester are too close together for fractional distillation to be conveniently possible. To prepare the unsymmetrical maleate/fumarate diester alone it is necessary to avoid the formation of a statistical mixture altogether by first preparing a monoester, by esterification with one alcohol (preferably octanol) under controlled conditions, and then subjecting the monoester to selective esterification with a derivative of the second alcohol (preferably hexanol) to give the unsymmetrical diester.

The first step, preparation of a pure monoester, may be achieved by heating the alcohol with maleic anhydride in a solvent such as toluene in the absence of an acid catalyst. A mixture of monoester and symmetrical diester is obtained and these can be separated without difficulty, for example, by recrystallisation from petroleum ether.

The second step must be carried out under conditions which avoid reversibility of the reaction, which would generate a statistical mixture of symmetrical and unsymmetrical diesters. Two methods have been developed, both of which involve reaction of an alkali metal salt of the monoester with an alkyl halide, preferably the bromide R'Br, to give the unsymmetrical diester with isomeric purity exceeding 92%.

According to the first method, an aqueous solution of an alkali metal (preferably potassium) salt of the monoester is reacted with a chloroform solution of the alkyl bromide in the presence of a phase transfer catalyst, for example, tetra-n-butyl ammonium bromide or iodide.

According to the second method, the alkyl bromide R'Br is reacted with the alkali metal salt of the monoester in a dipolar aprotic solvent, for example, dimethyl formamide, dimethyl sulphoxide, or hexamethyl phosphoric triamide. No catalyst is needed.

EXAMPLE 4

(i) Preparation of monooctyl maleate/fumarate

A mixture of octan-1-ol (250 ml, 1.59 mole) and toluene (200 mls) was placed in a 1-liter 3-necked round bottomed flask fitted with stirrer and condenser. Maleic anhydride (153 g, 1.56 mole) was added and the mixture was stirred under reflux for 2 hours. The toluene was evaporated in vacuo and the resulting oil diluted with 30/40 petroleum ether (1.5 liters). The mixture was filtered and left to crystallise at 4° C.

Two crops of crystals were obtained, the total yield being 311 g (87%). The crystals had a melting point of 37° C. and infra-red peaks at 1725 cm$^{-1}$ (C=O) and 1640 cm$^{-1}$ (C=C).

(ii) Preparation of hexyl/octyl maleate/fumarate

Monooctyl maleic/fumaric acid (88 g, 0.39 mole) was dissolved in chloroform (200 ml) and was stirred in a 1-liter Erlenmeyer (Quick Fit) flask, fitted with condenser, with a solution of potassium hydroxide (21 g, 0.38 mole) and tetrabutyl ammonium iodide (15 g, 0.04 mole) in 200 mls of water. To the stirred mixture was added hexyl bromide (64 g, 0.39 mole) and the two-phase mixture was stirred rapidly under reflux for 5 hours.

The chloroform layer was separated off, washed with sodium carbonate solution, then with water, and then dried over sodium sulphate. After filtering and evaporating the resulting oil was treated with 30/40 petroleum ether which precipitated the tetrabutyl ammonium iodide which could be reused. Filtration/evaporation yielded the crude product as an oil (77 g).

Distillation in vacuo removed 13.1 g hexyl bromide. The yield of undistilled material was 59.3 g (62% based on hexyl bromide). This material was shown, by means of a gas-liquid chromatograph with a flame ionisation detector, to have the following composition (by area): 0.7% diC$_6$ diester, 5% diC$_8$ diester, 93% unsymmetrical diester (76% maleate, 17% fumarate). It had infra-red peaks at 1640 cm$^{-1}$ (C=C) and 1725 cm$^1$ (C=O) and was also identified by $^1$H NMR and mass spectrometry.

(iii) Preparation of hexyl/octyl sulphosuccinate

Hexyl/octyl maleate/fumarate (50 g, 0.16 mole) was dissolved in methylated spirit (100 ml), and the mixture was stirred under reflux for 5 hours with a solution of sodium metabisulphite (60 g) in water (160 ml) in a 3-necked round bottom flask fitted with stirrer and condenser. The hot solution was filtered and set to crystallise. The crude crystals were filtered off, dried and extracted with boiling ethanol. The residual inorganics were filtered off. Evaporation of the filtrate yielded the product as a glassy solid (20 g) which failed to recrystallise from acetone or ethanol. This material contained 92% detergent-active material and 1.5% non-detergent organic matter. It had infra-red peaks at 1735 cm$^1$ (C=O) and 1210–1240 cm$^{-1}$ (SO$_3$Na) and was also identified by $^1$H NMR.

EXAMPLE 5

Preparation of pure $C_6/C_8$ sulphosuccinate (alternative method)

100 g (0.44 mole) of the product of Example 4(i) were dissolved in ethanol (200 ml) and treated with a solution of lithium hydroxide hydrate (20 g, 0.43 mole) in water (100 ml). The solvents were removed in vacuo and the resulting lithium salt was stirred at 90° C. with a solution of hexyl bromide (74 g, 0.44 mole) in dimethyl formamide (200 ml) for 5 hours. The solvent was removed in vacuo and the resulting oil was partitioned between water and ether; the dimethyl formamide washed out of the ether layer.

Analysis of the resulting oil (150 g) by means of a gas-liquid chromatograph with a flame ionisation detector indicated that the composition by area was as follows:

| % | Identity |
|---|---|
| 10 | monooctyl maleic/fumaric acid |
| 2 | dihexyl ester |
| 64.4 | $C_6/C_8$ unsymmetrical maleic ester |

| % | Identity |
|---|---|
| 17.6 | C₆/C₈ unsymmetrical fumaric ester |
| 2 | dioctyl ester |

The unwanted starting acid was removed by extracting an ether solution of the product with sodium carbonate solution. The purified material had infra-red peaks at 1640 cm$^{-1}$ (C=C) and 1725 cm$^{-1}$ (C=O) and was also identified by $^1$H NMR and mass spectrometry.

The product was converted to the corresponding sulphosuccinate as described in of Example 4(iii). The product was identical to that described in Example 4(iii).

EXAMPLE 6

Preparation of symmetrical dialkyl sulphosuccinates

Di-n-octyl sulphosuccinate was prepared by the procedure of Example 1, 260 g (2.0 moles) of octan-1-ol being used as the starting alcohol instead of the octanol/hexanol mix.

Di-n-hexyl sulphosuccinate and di-n-butyl sulphosuccinate were prepared by the same method, 203 g (2.0 moles) of hexan-1-ol and 146 g (2.0 moles) of butan-1-ol, respectively, being used instead of the octanol/hexanol mix.

EXAMPLES 7-15

The foaming performances of various sulphosuccinate mixtures according to the invention were measured by means of a modified Schlachter-Dierkes test based on the principle described in *Fette und Seifen* 1951, 53, 207. A 100 ml aqueous solution of each material tested, having a concentration of 0.05% active detergent, generally in 5°H or 24°H water (French hardness i.e. 5 or 24 parts calcium carbonate per 100,000 parts water), at 45° C., was rapidly oscillated using a vertically oscillating perforated disc within a graduated cylinder. After the initial generation of foam, increments (0.2 g) of soil (9.5 parts commercial cooking fat, 0.25 parts oleic acid, 0.25 parts stearic acid and 10 parts wheat starch in 120 parts water; in some cases, with 7 parts casein replacing 7 parts of water) were added at 15-second intervals (10 seconds' mild agitation and 5 seconds' rest) until the foam collapsed. The result was recorded as the number of soil increments (NSI score): a score difference of 6 or less is generally regarded as insignificant. Each result was typically the average of 3 or 4 runs.

EXAMPLE 7

The foaming performance of a sulphosuccinate mixture according to the invention was compared with that of a conventional commercially available dishwashing detergent-active material, namely a $C_{10}$-$C_{12}$ linear alkylbenzene sulphonate (Dobs (Trade Mark) 102 ex Shell), both alone and in the presence of alkyl ether sulphate at a weight ratio of 4:1. The alkyl ether sulphate was a $C_{12}$-$C_{15}$ primary alcohol 3EO sulphate (Dobanol (Trade Mark) 25-3A ex Shell). The sulphosuccinate mixture used was the C₆/C₈ ternary mixture (1:2:1) prepared in Example 1. The results are shown in Table 1.

TABLE 1

| | 5° H. | | 24° H. | |
|---|---|---|---|---|
| | Normal soil | Casein soil | Normal soil | Casein soil |
| Alkylbenzene sulphonate | 33 | 9 | 23 | 20 |
| Sulphosuccinate mix | 61 | 31 | 49 | 65 |
| Alkylbenzene sulphonate/alkyl ether sulphate | 52 | 9 | 60 | 34 |
| Sulphosuccinate mix/alkyl ether sulphate | 75 | 19 | 73 | 58 |

The sulphosuccinate mix alone is superior to the alkylbenzene sulphonate alone under all four sets of conditions, and is also better than alkylbenzene sulphonate/alkyl ether sulphate in both hard and soft water with casein soil. The addition of alkyl ether sulphate to the sulphosuccinate mix improves its performance still further, except in soft water with casein soil, and sulphosuccinate/alkyl ether sulphate is better than alkylbenzene sulphonate/alkyl ether sulphate under all four sets of conditions.

EXAMPLE 8

The performance of a binary mixture (according to the invention) of the di-n-octyl sulphosuccinate prepared in Example 6 and the n-octyl n-hexyl sulphosuccinate prepared in Example 4 was compared with the performances of the two constituent materials, and the results are shown in Table 2.

TABLE 2

| | 5° H. | | 24° H. | |
|---|---|---|---|---|
| Material (mole ratio where shown) | Normal soil | Casein soil | Normal soil | Casein soil |
| diC₈ | 40 | 28 | 1 | 37 |
| C₆/C₈ | 46 | 22 | 52 | 57 |
| diC₈ + C₆/C₈ (1:2) (predicted) | (44) | (24) | (35) | (50) |
| measured | 62 | 28 | 22 | 62 |

In soft water with normal soil, and in hard water with casein soil, the score of the mixture is substantially higher than would be predicted from the individual scores of the constituents. Furthermore, in soft water with normal soil, the performance is better than that of either of the constituent materials.

EXAMPLE 9

Example 8 was repeated using a range of ratios of the diC₈ material to the C₆/C₈ material. These tests were carried out on a different occasion, and using different apparatus, from those of Example 8, hence the slightly different scores for the individual materials. The results are shown in Table 3.

TABLE 3

| | 5° H. | | | | 24° H. | | | |
|---|---|---|---|---|---|---|---|---|
| | Normal Soil | | Casein Soil | | Normal Soil | | Casein Soil | |
| Mole Ratio diC₈:C₆/C₈ | Meas. | Pred. | Meas. | Pred. | Meas. | Pred. | Meas. | Pred. |
| diC₈ alone | 35 | — | 26 | — | 3 | — | 51 | — |
| 10:1 | 48 | (37) | 28 | (25) | 7 | (8) | 53 | (52) |
| 6:1 | 46 | (38) | 34 | (25) | 6 | (10) | 52 | (53) |
| 3:1 | 54 | (39) | 30 | (25) | 4 | (16) | 56 | (55) |

TABLE 3-continued

|  | 5° H. | | | | 24° H. | | | |
| --- | --- | --- | --- | --- | --- | --- | --- | --- |
|  | Normal Soil | | Casein Soil | | Normal Soil | | Casein Soil | |
| Mole Ratio diC$_8$:C$_6$/C$_8$ | Meas. | Pred. | Meas. | Pred. | Meas. | Pred. | Meas. | Pred. |
| 1:1 | 61 | (44) | 28 | (23) | 17 | (30) | 60 | (59) |
| 1:3 | 68 | (48) | 24 | (22) | 49 | (42) | 70 | (64) |
| 1:6 | 68 | (50) | 24 | (22) | 54 | (47) | 61 | (65) |
| 1:10 | 58 | (51) | 25 | (21) | 46 | (50) | 64 | (66) |
| C$_6$/C$_8$ alone | 53 | — | 21 | — | 55 | — | 68 | — |

Meas. = Measured
Pred. = Predicted

It will be noted that the scores are significantly higher than those obtained using the conventional dishwashing detergent system tested in Example 7.

It will also be observed that the performance at all ratios is outstandingly good in soft water with normal soil and in hard water with casein soil. Furthermore, in soft water with normal soil the measured performance at all ratios is considerably higher than the predicted performance, and at ratios of 1:1 and below is higher than that of either of the two constituent materials.

EXAMPLE 10

The foaming performance of the ternary mixture of di-n-octyl sulphosuccinate, n-hexyl n-octyl sulphosuccinate and di-n-hexyl sulphosuccinate, in a molar ratio of 1:2:1, prepared in Example 1 was compared with those of the individual materials and the results are shown in Table 4.

TABLE 4

|  | 5° H. | | 24° H. | |
| --- | --- | --- | --- | --- |
| Material (mole ratio where shown) | Normal soil | Casein soil | Normal soil | Casein soil |
| diC$_8$ | 40 | 28 | 1 | 37 |
| C$_6$/C$_8$ | 46 | 22 | 52 | 57 |
| diC$_6$ | 0 | 0 | 0 | 0 |
| diC$_8$ + C$_6$/C$_8$ + diC$_6$ | (33) | (18) | (26) | (38) |
| 1:2:1 (predicted) measured | 53 | 28 | 42 | 66 |

It will be seen that substantially better performances than expected can be obtained using the mixture, especially in soft water with normal soil and in hard water with casein soil, despite the presence of the di(n-hexyl) compound which alone has a performance too low to measure.

EXAMPLE 11

Example 10 was repeated using a wider range of water hardnesses. The results are shown in Table 5.

TABLE 5

|  | 5° H. | | 16° H. | | 24° H. | | 36° H. | |
| --- | --- | --- | --- | --- | --- | --- | --- | --- |
| Material | Normal Soil | Casein Soil | Normal Soil | Casein Soil | Normal Soil | Casein Soil | Normal Soil | Casein Soil |
| diC$_6$ | 0 | 0 | 0 | 0 | 0 | 0 | 0 | 0 |
| diC$_8$ | 35 | 26 | 2 | 36 | 3 | 51 | 3 | 24 |
| C$_6$/C$_8$ | 53 | 21 | 46 | 44 | 55 | 68 | 54 | 84 |
| Mixture: |  |  |  |  |  |  |  |  |
| Measured | 61 | 31 | 42 | 52 | 49 | 65 | 24 | 54 |
| (Predicted) | (35) | (17) | (27) | (30) | (25) | (47) | (27) | (48) |

These tests were carried out on a separate occasion, and using different apparatus, from those of Example 10, hence the slightly different scores for the diC$_8$ and C$_6$/C$_8$ compounds.

The same trends as in Example 10 can be seen at the three lower water hardnesses. At 36°H, however, there is virtually no difference between predicted and measured scores.

EXAMPLE 12

The performance of the ternary mixture of di-n-octyl sulphosuccinate, n-butyl n-octyl sulphosuccinate and di-n-butyl sulphosuccinate, in a molar ratio of 1:2:1, prepared in Example 2 was compared with those of the individual materials and the results are shown in Table 6.

TABLE 6

|  | 5° H. | | 24° H. | |
| --- | --- | --- | --- | --- |
| Material (mole ratio where shown) | Normal soil | Casein soil | Normal soil | Casein soil |
| diC$_8$ | 40 | 28 | 1 | 37 |
| C$_4$/C$_8$ | 21 | 13 | 14 | 28 |
| diC$_4$ | 0 | 0 | 0 | 0 |
| diC$_8$ + C$_4$/C$_8$ + diC$_4$ | (21) | (14) | (7) | (23) |
| 1:2:1 (predicted) measured | 26 | 24 | 7 | 53 |

It will be seen that in the three cases where the individual performances of the separate constituents are reasonable, the mixture gives a better result than would be predicted. In hard water with normal soil, where none of the individual constituents gives an acceptable performance, the mixture does not offer any improvement.

EXAMPLE 13

A mixed sulphosuccinate material was prepared by the procedure of Example 1 using the following mix of alcohols: 1 part (molar) n-butanol, 1 part n-hexanol and 2 parts n-octanol. The resulting product contained diC$_8$, diC$_6$, diC$_4$, C$_6$/C$_8$, C$_4$/C$_6$ and C$_4$/C$_8$ sulphosuccinates.

The foaming performance was as shown in Table 7.

TABLE 7

|  | 5° H. | | 24° H. | |
|---|---|---|---|---|
|  | Normal soil | Casein soil | Normal soil | Casein soil |
| (predicted) | (30) | (14) | (18) | (33) |
| measured | 51 | 31 | 28 | 60 |

In calculating the predicted performance, the score of the $C_4/C_6$ compound, which had not been separately measured, was assumed to be zero; this is consistent with the measured scores of zero for both the $diC_4$ and $diC_6$ compounds.

EXAMPLE 14

In this experiment the foaming performance of a sulphosuccinate mixture according to the invention in admixture with another detergent active material conventionally used in dishwashing (an alkyl ether sulphate) was investigated. The sulphosuccinate mixture used was the $C_6/C_8$ ternary mixture prepared in Example 1 (mole ratio 1:2:1), the alkyl ether sulphate was Dobanol 25-3A as used in Example 7, and the weight ratio of total sulphosuccinate to alkyl ether sulphate was 4:1. The performance of this system was compared with those of corresponding mixtures of the individual sulphosuccinates with the alkyl ether sulphate at the same weight ratio of 4:1, the results being shown in Table 8; only normal soil was used in these tests.

It will be noted, by comparison with Example 11, that the presence of the ether sulphate gives an improved performance in both hard and soft water.

TABLE 8

| Sulphosuccinate material | 5° H. | 24° H. |
|---|---|---|
| $diC_8$ | 48 | 23 |
| $diC_6$ | 12 | 15 |
| $C_6/C_8$ | 48 | 87 |
| Mixture: | | |
| measured | 75 | 73 |
| (predicted) | (39) | (53) |

EXAMPLE 15

In this experiment the effect of varying the ratio of sulphosuccinate mixture to alkyl ether sulphate was investigated. The sulphosuccinate mixture was again the $C_6/C_8$ ternary mixture (1:2:1) and the alkyl ether sulphate was again Dobanol 25-3A. The results are shown in Table 9.

Good scores were obtained at all ratios, all being significantly higher than the predicted scores. For good performance in both hard and soft water ratios of 1:1, 2:1 and 4:1 appear to be optimal.

TABLE 9

| Material/ weight ratio | 5° H. | | 24° H. | |
|---|---|---|---|---|
|  | Measured | (Predicted) | Measured | (Predicted) |
| Sulpho-succinate alone | 61 | — | 49 | — |
| 20:1 | 87 | (59) | 59 | (48) |
| 12:1 | 88 | (59) | 57 | (48) |
| 8:1 | 81 | (58) | 61 | (47) |
| 4:1 | 75 | (55) | 73 | (46) |
| 2:1 | 69 | (51) | 93 | (43) |
| 1:1 | 53 | (45) | 93 | (40) |
| 1:2 | 43 | (40) | 58 | (38) |
| 1:4 | 36 | (36) | 44 | (35) |
| Ether sulphate alone | 30 | — | 32 | — |

EXAMPLE 16

In this experiment the dishwashing performance of a dialkyl sulphosuccinate/alkyl ether sulphate mixture was compared with that of an alkyl benzene sulphonate/alkyl ether sulphate mixture using a plate washing test.

In the test, plates soiled with a starch/fat/fatty acid mixture were washed in a standard manner with 5 liters of test solution (total concentration 0.4 g/liter in 5°H or 24° H in water) in a bowl, until only a third of the surface of the solution in the bowl was covered with foam. The number of plates washed before this arbitrary endpoint was reached was taken as an indicator of dishwashing performance.

The composition according to the invention to be used in this test was a 4:1 by weight mixture of the statistical mixture prepared in Example 1 and the alkyl ether sulphate (Dobanol 25-3A) used in Example 7; and the comparison composition was a 4:1 by weight mixture of the alkyl benzene sulphonate (Dobs 102) used in Example 7 and the alkyl ether sulphate (Dobanol 25-3A) used in Example 7. The results, which clearly show the superiority of the sulphosuccinate-based composition, are shown in Table 10.

TABLE 10

|  | Number of plates washed | |
|---|---|---|
|  | 5° H. | 24° H. |
| Sulphosuccinate/alkyl-ether sulphate | 51 | 54 |
| Alkylbenzene sulphonate/alkyl ether sulphate | 33 | 28 |

EXAMPLE 17

In this experiment the dishwashing performance of a series of dilute solutions of the statistical mixture prepared in Example 1 was evaluated using a slightly different plate washing test method.

In this test, plates soiled with a wheat flour/soya oil/oleic acid/stearic acid soil were each prewetted with 10 ml of 4°H water and then washed, by the direct application thereto of a small quantity (2.5 ml) of the test product on a sponge prewetted with 26 ml of 4°H water. The number of plates washed, using a set procedure, before foam collapse occurred was taken as an indicator of dishwashing performance.

Dilute aqueous solutions of the sulphosuccinate mix at three different concentrations were prepared and tested, and for comparison three solutions of a linear $C_{10}$–$C_{13}$ alkylbenzene sulphonate (ex Deten, Brazil) were also prepared and tested. The results are shown in Table 11.

TABLE 11

|  | Number of plates washed | |
|---|---|---|
| Concentration (weight %) | Sulphosuccinate Mix | Alkylbenzene Sulphonate |
| 11.5 | 20 | 12 |
| 5.0 | 14 | 8 |

TABLE 11-continued

| Concentration (weight %) | Number of plates washed | |
|---|---|---|
| | Sulphosuccinate Mix | Alkylbenzene Sulphonate |
| 2.5 | 10 | (not tested) |

From these results it can be inferred by interpolation that a solution of the sulphosuccinate mix having a concentration of about 3.5% would have a performance equivalent to that of the 11.5% alkylbenzene sulphonate solution.

EXAMPLE 18

In this Example the dishwashing performance of a sulphosuccinate/alkyl ether sulphate mixture was compared with that of an alkylbenzene sulphonate/alkyl ether sulphate mixture, using a third test method.

In this test, the plates used were soild with a corn oil/oleic acid/stearic acid/rice starch soil, and each was prewetted with 7 ml of 5°H water. A sponge was dipped into 50 ml of a 4% solution in 5° H water) of the test product and used to wash the plates using a set procedure, the number of plates washed before foam collapse occurred being taken as an indicator of dishwashing performance.

The products according to the invention used for this test were dilute aqueous solution of a 4:1 by weight mixture of the statistical mixture of Example 1 with the ether sulphate used in Example 7 (Dobanol 25-3A). The comparison products were dilute aqueous solutions of a 4:1 by weight mixture of a $C_{11}-C_{14}$ linear alkylbenzene sulphonate (ex Mitsubishi, Japan) and a $C_{11}-C_{13}$ oxo alcohol 3EO sulphate (Synperonic (Trade Mark) 3S-60 ex ICI). The test results are shown in Table 12.

TABLE 12

| Total Concentration (by weight %) | Number of plates washed | |
|---|---|---|
| | Sulphosuccinate Mix | Alkylbenzene Sulphonate |
| 15 | (not tested) | 17 |
| 7.5 | 24 | 10 |
| 3.75 | 14 | 7 |

Again, it can be inferred by interpolation that a sulphosuccinate/ether sulphate system having a total concentration of 5.5% by weight would have a performance equivalent to that of a 15% by weight alkylbenzene sulphonate/ether sulphate system.

EXAMPLE 19

The efficacy of a sulphosuccinate mix according to the invention as a shampoo detergent was investigated in the following experiment, in which the foaming capacity of the mix in the presence of simulated sebum was compared with those of some known shampoo detergents. The sulphosuccinate mix used was the $C_6/C_8$ statistical mixture prepared in Example 1, and the simulated sebum had the following composition:

| | Weight % |
|---|---|
| Triolein | 35.0 |
| Tristearin | 10.0 |
| Oleic acid | 10.0 |
| Stearic acid | 5.0 |
| Squalene | 35.0 |
| Cholesterol | 5.0 |

For each material tested, a 12% solution in 14°H water was prepared (this simulates a typical shampoo composition in the bottle) and was then diluted by a factor of 9 (this simulates the dilution of a shampoo by the consumer immediately before and during application to the hair). 1 g of artificial sebum was added to a fixed volume (180 ml) of each diluted (1.33%) solution, mechanical agitation was effected using a food mixer rotating at 600 rpm, and the volume of foam generated after 2 minutes was measured. The results are shown in Table 13.

TABLE 13

| Detergent-active Material | Foam Volume (ml) |
|---|---|
| Dodecyl benzene sulphate | 40 |
| Monoalkyl sulphosuccinate (Condanol (Trade Mark) SBFA/3) | 110 |
| Sodium lauryl ether (2EO) sulphate | 130 |
| Monoethanolamine lauryl sulphate | 200 |
| Sulphosuccinate mix | 240 |

It will be seen then in this in vitro test the sulphosuccinate mix of the invention produces significantly higher volumes of foam than do the conventional shampoo detergents sodium lauryl ether sulphates and monoethanolamine lauryl sulphate. The monoalkyl sulphosuccinate performs substantially worse than the dialkyl sulphosuccinate mix of the invention.

EXAMPLE 20

Using the procedure of Example 19, the effect of diluting the initial solution from 12% to 6% was investigated. The results are shown in Table 14.

TABLE 14

| Detergent-active Material | Concentration of initial solution (weight %) | Foam Volume (ml) |
|---|---|---|
| $C_6/C_8$ sulphosuccinate mix | 12% | 250 |
| | 6% | 225 |
| Sodium lauryl ether sulphate | 12% | 120 |

The results show that even using half the concentration of detergent-active material in the initial solution, a result significantly better than that for the conventional material at the higher concentration is obtained.

EXAMPLE 21

In this experiment the removal of clay soil from fabrics by a material according to the invention was compared with that by a conventional fabric washing detergent-active agent, in a tergotometer test. The material according to the invention was the statistical mixture prepared in Example 1, and the comparison material was a linear $C_{10}-C_{15}$ alkylbenzene sulphonate (Dobs (Trade Mark) 055 ex Shell).

In each case a wash liquor (500 ml) was prepared containing, in demineralised water, 0.1 liter or 0.2 g/liter of the detergent-active material and 1 g/liter of sodium mataborate tetrahydrate buffer. 10 g of illite-clay-soiled polyester cotton test cloth pieces were added and the liquor was agitated at 90 cycles/minutes for 30 minutes at 25° C. The amount of clay soil removed from the test cloth was calculated from the reflectance increase, as measured by means of a Carl Zeiss Elrepho Reflectometer.

The results were as follows:

| Detergent-active | Soil removed (%) | |
|---|---|---|
| material | 0.1 g/l | 0.2 g/l |
| Sulphosuccinate | 61 | 68 |
| Alkylbenzene sulphonate | 53 | 63 |

We claim:

1. A detergent composition comprising
(a) one or more compounds of the formula I

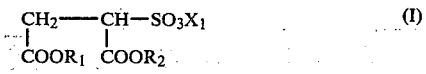

wherein each of $R_1$ and $R_2$, which may be the same or different, represents an alkyl group having from 7 to 9 carbon atoms, and $X_1$ represents a solubilising monovalent cation or 1/m of a solubilising m-valent cation, and
(b) one or more compounds of the formula II

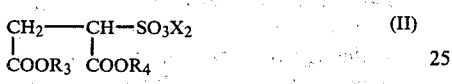

wherein one of $R_3$ and $R_4$ represents an alkyl group having from 7 to 9 carbon atoms and the other represents an alkyl group having from 3 to 6 carbon atoms, and $X_2$ represents a solubilising cation which may be the same as or different from $X_1$ the mole ratio of component (a) to component (b) being within the range from 10:1 to 1:10.

2. The detergent composition of claim 1, wherein the total number of carbon atoms in the groups $R_3$ and $R_4$ is at least 12.

3. The detergent composition of claim 1, wherein at least one of the groups $R_1$, $R_2$, $R_3$ and $R_4$ is a straight-chain alkyl group.

4. The detergent composition of claim 1, wherein in component (a) the groups $R_1$ and $R_2$ are the same.

5. The detergent composition of claim 1, wherein the longer of the groups $R_3$ and $R_4$ in component (b) is the same as at least one of the groups $R_1$ and $R_2$ in component (a).

6. The detergent composition of claim 5, wherein the longer of the groups $R_3$ and $R_4$ in component (b) and both groups $R_1$ and $R_2$ in component (a) are the same.

7. A detergent composition of claim 5, wherein component (a) comprises a di($C_8$ alkyl) sulphosuccinate and component (b) is selected from the group consisting of ($C_4$ alkyl) ($C_8$ alkyl) sulphosuccinates, ($C_6$ alkyl) ($C_8$ alkyl) sulphosuccinates, and mixtures thereof.

8. The detergent composition of claim 1, which additionally comprises
(c) one or more compounds of the formula III

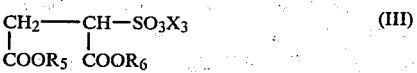

wherein each of $R_5$ and $R_6$, which may be the same or different, represents an alkyl group having from 3 to 6 carbon atoms, and $X_3$ represents a solubilising cation which may be the same as or different from $X_1$ and/or $X_2$.

9. The detergent composition of claim 8, wherein component (c) is present in an amount not exceeding 50 mole percent, based on the total amount of components (a), (b) and (c).

10. The detergent composition of claim 8, wherein in component (c) the groups $R_5$ and $R_6$ are straight-chain alkyl groups.

11. The detergent composition as claimed in claim 8, wherein in component (c) the groups $R_5$ and $R_6$ are the same.

12. The detergent composition of claim 8, wherein at least one of the groups $R_5$ and $R_6$ in component (c) is the same as the shorter of the groups $R_3$ and $R_4$ in component (b).

13. The detergent composition of claim 8, wherein component
(a) has the formula IV

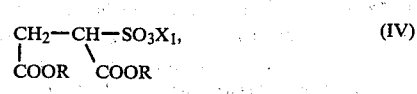

component (b) has the formula V

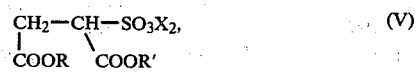

and/or the formula V'

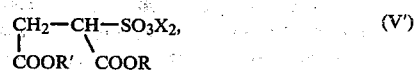

and component (c) has the formula VI

wherein $X_1$ and $X_2$ have the meanings given in claim 1, $X_3$ has the meaning given in claim 10, R is a ($C_7$–$C_9$) alkyl group and R' is a ($C_3$–$C_6$) alkyl group.

14. The detergent composition of claim 13, wherein R is a $C_8$ alkyl group and $R_2$ is selected from the group consisting of $C_4$ and $C_6$ alkyl groups.

15. The detergent composition of claim 13, wherein the mixture of components (a), (b) and (c) has been prepared by a process which includes the step of esterifying an sulphosuccinic acid with a mixture of the alcohols ROH and R'OH or suitable derivatives thereof.

16. The detergent composition of claim 13, wherein the mixture of components (a), (b) and (c) has been prepared by a process which includes the steps of esterifying a material selected from the group consisting of maleic anhydride, maleic acid, fumaric acid, and suitable derivatives thereof with a mixture of the alcohols ROH and R'OH or suitable derivatives thereof followed by sulfonation of the resultant esters.

17. The detergent composition of claim 1, which additionally contains one or more detergent-active agents selected from the group consisting of anionic, nonionic, cationic, zwitterionic or amphoteric detergent-active agents.

18. The detergent composition of claim 17, which contains at least one detergent-active agent selected from the group consisting of alkylbenzene sulphonates, secondary alkyl sulphonates, alpha-olefin sulphonates, alkyl glyceryl ether sulphonates, primary and secondary alkyl sulphates, alkyl ether sulphates, fatty acid ester sulphonates, alcohol ethoxylates and propoxylates, alkyl phenol ethoxylates and propoxylates, alkyl amine oxides, and fatty acid mono- and dialkanolamides.

19. The detergent composition of claim 17, wherein the weight ratio of total sulphosuccinate to other detergent-active material is within the range of from 1:4 to 20:1.

20. The detergent composition of claim 17, wherein the weight ratio of total sulphosuccinate to other detergent-active material is within the range of from 1:1 to 12:1.

21. The detergent composition of claim 1, which is a liquid.

22. The detergent composition of claim 21, which is in the form of an aqueous solution having a total content of detergent-active material within the range of from 2 to 60% by weight.

23. The detergent composition of claim 22, which includes a viscosity control system comprising at least one material selected from the group consisting of lower alkanols, urea, and lower alkylbenzene sulphonates.

* * * * *